United States Patent [19]

Winter et al.

[11] 4,232,024
[45] Nov. 4, 1980

[54] 1-OXO-1H-PYRIMIDO[6,1-b]BENZ-THIAZOLE DERIVATIVES

[75] Inventors: Werner Winter, Heppenheim; Herman Hindermayr, Mannheim; Egon Roesch, Mannheim; Androniki Roesch, Mannheim; Otto-Henning Wilhelms, Heddesheim, all of Fed. Rep. of Germany

[73] Assignee: Boehringer Mannheim GmbH, Mannheim, Fed. Rep. of Germany

[21] Appl. No.: 15,372

[22] Filed: Feb. 26, 1979

[30] Foreign Application Priority Data

Mar. 13, 1978 [DE] Fed. Rep. of Germany ....... 2810863

[51] Int. Cl.³ .................. A61K 31/505; C07D 513/04
[52] U.S. Cl. .................................... 424/251; 544/247; 544/250
[58] Field of Search ................. 544/250, 247; 424/251

[56] References Cited

U.S. PATENT DOCUMENTS 3,538,086  11/1970  Mair et al. ............................ 544/247
4,041,163  8/1977  Bindra et al. ........................ 544/250

FOREIGN PATENT DOCUMENTS 2126148  12/1972  Fed. Rep. of Germany .

Primary Examiner—Paul M. Coughlan, Jr.
Attorney, Agent, or Firm—Sprung, Felfe, Horn, Lynch & Kramer

[57] ABSTRACT

Anti-allergy novel 1-oxo-1H-pyrimido[6,1-b]benzthiazole derivatives of the formula

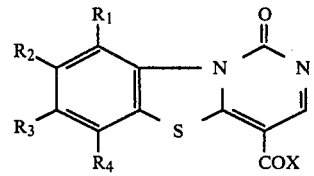

wherein
$R_1$, $R_2$, $R_3$ and $R_4$ each independently is hydrogen, halogen, hydroxy, nitro, trifluoromethyl, or lower alkyl, alkoxy or alkylthio, or
$R_2$ and $R_3$ together are alkylenedioxy, and
X is hydroxy, alkoxy or tetrazolyl-5-amino, or salts thereof, as well as their production by saponification of

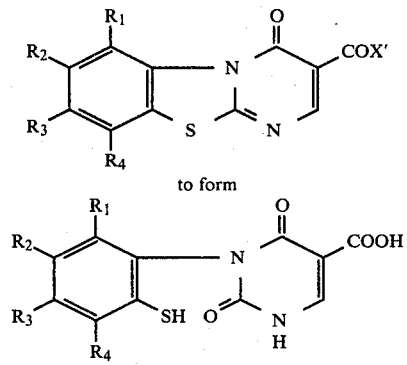

or tautomers thereof, followed by acidification.

10 Claims, No Drawings

1-OXO-1H-PYRIMIDO[6,1-b]BENZTHIAZOLE DERIVATIVES

The present invention is concerned with 1-oxo-1H-pyrimido[6,1-b]benzthiazole derivatives, with the preparation thereof and with pharmaceutical compositions containing them.

Thus, according to the present invention, there are provided 1-oxo-1H-pyrimido[6,1-b]benzthiazole derivatives of the general formula:

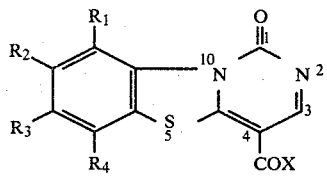

wherein $R_1$, $R_2$, $R_3$ and $R_4$, which can be the same or different, are hydrogen or halogen atoms, hydroxyl or nitro groups, trifluoromethyl radicals or lower straight-chained or branched alkyl, alkoxy or alkylthio radicals or $R_2$ and $R_3$ can together represent an alkylenedioxy radical and X is a hydroxyl group or an alkoxy or tetrazolyl-5-amino radical; and the pharmacologically acceptable salts thereof.

The salts of compounds of general formula (I) can be, for example, inorganic salts, preferably alkali metal salts, or organic salts, preferably of primary or secondary amines.

When $R_1$, $R_2$, $R_3$ and $R_4$ are lower, straight-chained or branched alkyl, alkoxy or alkylthio radicals and when X is an alkoxy radical, these radicals are to be understood to contain up to 6 carbon atoms and preferably up to 4 carbon atoms, the methyl, ethyl, n-propyl, isopropyl and tert.-butyl radicals, as well as the corresponding alkoxy and alkylthio radicals, being especially preferred.

When $R_2$ and $R_3$ together represent an alkylenedioxy radical, it preferably contains up to 3 carbon atoms, the methylenedioxy radical being especially preferred.

The halogen atoms are to be understood to include fluorine, chlorine and bromine atoms, chlorine atoms being especially preferred.

We have found that the new 1-oxo-1H-pyrimido[6,1-b]benzthiazole derivatives according to the present invention display, when administered parenterally or also perorally, an outstanding antiallergic action, as can be demonstrated in the pharmacological test of passive cutaneous anaphylaxis (PCA test) in vivo on rats. The inhibitory potency of this class of compounds can also be convincingly demonstrated in vitro on the basis of antigen-induced mast cell granulation. Therefore, the new compounds according to the present invention are especially advantageous for combating allergic diseases, for example, allergic asthma, hayfever and urticaria. Furthermore, they possess anti-oedematous and anti-inflammatory properties.

The new compounds according to the present invention can also be further reacted in various ways to give compounds which are also pharmacologically active. Therefore, they are also valuable intermediates for the preparation of pharacologically-active compounds.

The new compounds according to the present invention can be prepared, for example, by hydrolyzing a 4-oxo-4H-pyrimido[2,1-b]benzthiazole of the general formula:

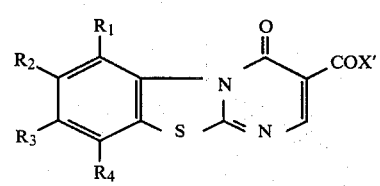

wherein $R_1$, $R_2$, $R_3$ and $R_4$ have the same meanings as above and X' is a lower alkoxy radical or a hydroxyl group, with excess base to give a solution containing a tautomeric equilibrium mixture of 1-(2-mercaptophenyl)-pyrimidine-2,6-diones of the general formulae:

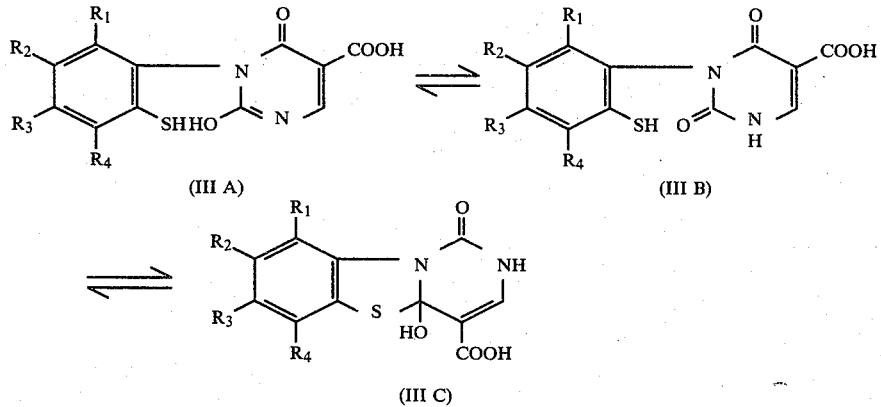

wherein $R_1$, $R_2$, $R_3$ and $R_4$ have the same meanings as above, or alkali metal salts thereof, which compounds are then cyclized under acidic reaction conditions, by the spitting off of water, to give compounds of general formula (I), in which X is a hydroxyl group, whereafter, if desired, in any desired sequence, the carboxylic acid thus obtained is converted in known manner into an ester or tetrazolyl-5-amide of general formula (I), in which X is an alkoxy or tetrazolyl-5-amino radical; when one of the symbols $R_1$, $R_2$, $R_3$ and $R_4$ is to represent a nitro group, this is subsequently introduced, a particular substituent $R_1$, $R_2$, $R_3$, $R_4$ or X can be converted into a different substituent $R_1$, $R_2$, $R_3$, $R_4$ and X and/or a carboxylic acid or tetrazolylamide obtained of general formula (I) can be converted into pharmacologically acceptable salts.

Starting compounds of general formula (II) are known (cf., for example D. W. Dunwell, D. Evans, J. Chem. Soc. (C), 2094, 1971) and can be prepared analogously to known processes. Thus, for example, a 2-aminobenzthiazole of the general formula:

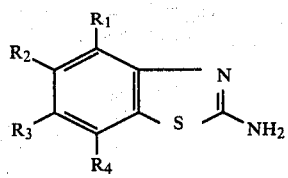

(IV), wherein $R_1$, $R_2$, $R_3$ and $R_4$ have the same meanings as above, can be reacted with an ethoxymethylenemalonic acid ester, preferably with diethyl ethoxymethylenemalonate, to give an aminomethylene derivative of the general formula:

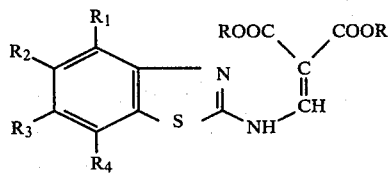

(V)

wherein $R_1$, $R_2$, $R_3$ and $R_4$ have the same meanings as above and R is a lower alkyl radical and preferably a methyl or ethyl radical, which can be cyclized in known manner to give a carboxylic acid ester of general formula (II) (X'=alkoxy). According to the procedure described by Alaimo (J. Het. Chem., 10, 769/1973), a carboxylic acid ester of general formula (II) (X'=alkoxy) can be converted into a carboxylic acid of general formula (II) (X'=hydroxyl) by acidic or alkaline saponification.

Surprisingly, we have found that in the case of the carboxylic acids and also of the carboxylic acid esters of general formula (II), when these are saponified with excess alkali and subsequently again treated with an acid, the original ring system of general formula (II) is not reformed: on the contrary, a rearrangement takes place to give the new ring system of the compounds according to the present invention of general formula (I).

The process according to the present invention is advantageously carried out by mixing a compound of general formula (II) with an excess of a base, preferably with an aqueous solution of sodium hydroxide or of potassium hydroxide, to which can be added an appropriate organic water-miscible solvent, for example, methanol or ethanol, whereafter the reaction mixture obtained is heated for about 0.5 to 2 hours. Fission of a sulphur-carbon bond of the benzthiazoles results in the formation of the new intermediates of general formulae (IIIA), (IIIB) and (IIIC) which are present in tautomeric equilibrium. The intermediate of general formula (IIIB) can be obtained without difficulty by careful neutralization of the reaction solution with an appropriate acid, preferably with dilute hydrochloric acid.

Cyclization of compounds of general formula (III), which requires a strongly acidic reaction medium which splits off water, can be achieved in a large variety of ways. For example, the pyrimidinediones of general formula (III) can be heated with a polyphosphoric acid or with a polyphosphoric acid ester, preferably at a temperature of about 120° C. Cyclization can also be readily carried out by heating in dioxane, after the addition of a solution of hydrochloric acid in dioxane, or in 20% or concentrated hydrochloric acid. It is particularly advantageous to use a strongly acidic ion exchanger, for example Amberlite IRC 120 or Amberlyst 15, in the presence of an appropriate solvent, for example dioxane or dimethylformamide, at ambient temperature or possibly at an elevated temperature.

The strongly acidic agent splitting off water can also be a boron trifluoride-acetic acid complex or also a Lewis acid, for example aluminum trichloride, in an organic solvent, for example chloroform.

When compounds of general formula (III) are heated under reflux in alcoholic hydrochloric acid, in addition to the ring closure, esterification to give carboxylic acids of general formula (I), in which X is an alkoxy radical, also takes place.

As a simplified variant of the process according to the present invention, in some cases it is possible to omit the isolation of the intermediates of general formula (III). For this purpose, directly after the alkaline fission of the compounds of general formula (II), ring closure to give the compounds according to the present invention of general formula (I) can be achieved by adding an excess of a mineral acid.

Furthermore, we have, surprisingly, also found that the known aminomethylene compounds (V) can be converted directly into the compounds (I) according to the present invention when the compounds (V) are treated under the same alkaline conditions as are required for the starting materials of general formula (II). There are thus formed intermediates of general formula (III) which are then worked up in the above-described manner to give compounds of general formula (I).

An especially advantageous variant for carrying out the process according to the present invention consists in condensing a 2-aminobenzthiazole (IV) in known manner with an ethoxymethylenemalonic acid ester in an appropriate solvent to give an enamine (V), preferably at a temperature of about 100° to 120° C., and thereafter cyclizing at an elevated temperature, preferably of about 200° to 240° C., to give a 4-oxo-4H-pyrimido[2,1-b]benzthiazole of general formula (II), whereafter, without isolating the compound of general formula (II), alkaline fission is carried out in a two-phase reaction mixture, with the formation of an intermediate product (III) which is subsequently worked up to give the desired end product of general formula (I).

This process variant can be advantageously modified in that the solvent suitable for the ring closure of the compounds (V) is, after cyclization has taken place, substantially evaporated off and subsequently, without isolating the pyrimido[2,1-b]benzthiazole of general formula (II), alkaline fission is carried out in a single phase reaction mixture, preferably in an alcoholic solution of an alkali metal hydroxide, with the formation of an intermediate product of general formula (III).

Esterification of a carboxylic acid of general formula (I) obtained according to one of the above-described variants is preferably carried out in the presence of an acidic catalyst, for example, hydrogen chloride, sulphuric acid, p-toluenesulphonic acid or a strongly acidic ion exchanger. It is also possible to react an alkali metal salt of the carboxylic acid or a salt thereof with an organic base with an alkyl halide in an appropriate solvent, for example hexamethyl phosphoric acid triamide. Transesterification, on the other hand, usually requires the addition of a small amount of a basic substance, for example of an alkali metal or alkaline earth metal hydroxide or of an alkali metal alcoholate.

For the condensation of a carboxylic acid of general formula (I) with 5-aminotetrazole, there are used the methods of amidation known from the literature, use preferably being made of 1,1'-carbonyldiimidazole or of dicyclohexylcarbodiimide. However, the carboxyl group can also be converted in known manner into a reactive derivative, for example an acid halide, an active ester or a mixed anhydride and this then reacted with 5-aminotetrazole.

For the preparation of salts with pharmacologically acceptable organic or inorganic bases, for example sodium hydroxide, potassium hydroxide, calcium hydroxide, ammonium hydroxide, methylglucamine, morpholine or ethanolamine, the carboxylic acids are reacted with the appropriate bases. Mixtures of carboxylic acids with appropriate alkali metal carbonates or bicarbonates can also be used.

For the preparation of medicaments, the new compounds according to the present invention are mixed in the usual manner with appropriate pharmaceutical carrier materials and aroma, flavoring and coloring materials and formed, for example, into tablets or dragees or, with the addition of appropriate adjuvants, suspended or dissolved in water or an oil, for example olive oil.

The new compounds according to the present invention can be administered orally or parenterally in liquid or solid form. As injection medium, it is preferred to use water which contains the stabilizing agents, solubilizing agents and/or buffers conventional in the case of injection solutions. Additives of this type include, for example, tartrate and borate buffers, ethanol, dimethyl sulphoxide, complex-forming agents (such as ethtylenediamine-tetraacetic acid), high molecular weight polymers (such as liquid polyethylene oxide) for viscosity regulation or polyethylene derivatives of sorbitol anhydrides.

Solid carrier materials include, for example, starch, lactose, mannitol, methyl cellulose, talc, highly dispersed silicic acid and high molecular weight polymers (such as polyethylene glycols).

Compositions suitable for oral administration can, if desired, contain flavoring and/or sweetening agents. For external application, the new compounds according to the present invention can also be employed in the form of powders or salves, for which purpose they are mixed, for example, with powdered, physiologically acceptable diluents or conventional salve bases.

Apart from the compounds mentioned in the specific examples, the following compounds are also preferred according to the present invention:

7-t-butyl-1-oxo-1H-pyrimido[6,1-b]benzthiazole-4-carboxylic acid
7-fluoro-1-oxo-1H-pyrimido[6,1-b]benzthiazole-4-carboxylic acid
8-trifluoromethyl-1-oxo-1H-pyrimido[6,1-b]benzthiazole-4-carboxylic acid
N-(5-tetrazolyl)-7,8-dimethyl-1-oxo-1H-pyrimido[6,1-b]-benzthiazole-4-carboxamide
N-(5-tetrazolyl)-7-methyl-1-oxo-1H-pyrimido[6,1-b]benzthiazole-4-carboxamide.
N-(5-tetrazolyl)-7-hydroxy-1-oxo-1H-pyrimido[6,1-b]benzthiazole-4-carboxamide
N-(5-tetrazolyl)-7-ethoxy-1-oxo-1H-pyrimido[6,1-b]benzthiazole-4-carboxamide
N-(5-tetrazolyl)-7,8-methylenedioxy-1-oxo-1H-pyrimido[6,1-b]benzthiazole-4-carboxamide
N-(5-tetrazolyl)-7-chloro-1-oxo-1H-pyrimido[6,1-b]benzthiazole-4-carboxamide
N-(5-tetrazolyl)-8-methoxy-1-oxo-1H-pyrimido[6,1-b]benzthiazole-4-carboxamide
N-(5-tetrazolyl)-6,8-dimethyl-7-methoxy-1-oxo-1H-pyrimido-[6,1-b]benzthiazole-4-carboxamide
N-(5-tetrazolyl)-7,8-dimethoxy-1-oxo-1H-pyrimido[6,1-b]-benzthiazole-4-carboxamide
N-(5-tetrazolyl)-7-methylthio-1-oxo-1H-pyrimido[6,1-b]-benzthiazole-4-carboxamide
N-(5-tetrazolyl)-7-isopropyl-1-oxo-1H-pyrimido[6,1-b]-benzthiazole-4-carboxamide
N-(5-tetrazolyl)-7-t-butyl-1-oxo-1H-pyrimido[6,1-b]benzthiazole-4-carboxamide
N-(5-tetrazolyl)-7-fluoro-1-oxo-1H-pyrimido[6,1-b]benzthiazole-4-carboxamide
-N-(5-tetrazolyl)-8-trifluoromethyl-1-oxo-1H-pyrimdio-[6,1-b]benzthiazole-4-carboxamide
N-(5-tetrazolyl)-8-nitro-1-oxo-1H-pyrimido[6,1-b]benzthiazole-4-carboxamide.

The following examples are given for the purpose of illustrating the present invention. The structure of the compounds has been verified by CHNS analyses and IR, UV, EMR and mass spectra. Some characterizing physical data are also given in the individual examples.

Although, in most cases, it does not appear to be necessary to isolate the particular intermediates, in the following examples, for the additional characterisation of the structure of the end products of general formula (I), such compounds are also described with their physical data.

EXAMPLE 1

7-Methoxy-1-oxo-1H-pyrimido[6,1-b]benzthiazole-4-carboxylic acid.

A.

1-(2-Mercapto-4-methoxyphenyl)-5-carboxypyrimidine-2,6-dione.

Variant I.

4.5 g. Ethyl 8-methoxy-4-oxo-4H-pyrimido[2,1-b]-benzthiazole-3-carboxylate (prepared by the method described by Alaimo, J. Het. Chem., 10, 769/1973) are mixed with a mixture of 75 ml. 10% aqueous sodium hydroxide solution and 25 ml. ethanol and heated under reflux for 30 minutes. After neutralizing the reaction mixture with 2 N hydrochloric acid, 1-(2-mercapto-4-methoxyphenyl)-5-carboxypyrimidine-2,6-dione precipitates out. The yield is 3.5 g. (80% of theory); m.p. 266°–267° C. (decomp.).

UV spectrum: pH 7 $\lambda_{max.}=268$ m$\mu$ pH 1 $\lambda_{max.}=274$ m$\mu$ pH 13 $\lambda_{max.}=293$ m$\mu$ Mass spectrum: M+ 294, m/e 261

Variant II.

25 g. Diethyl N-(6-methoxybenzthiazol-2-yl)-aminomethylenemalonate are introduced into a solution of 36 g. sodium hydroxide, 360 ml. water and 120 ml. ethanol which has been heated to 70° C. and the reaction mixture is heated under reflux for 30 minutes. A part of the ethanol is then removed in vacuo, filtered and, after cooling, the filtrate is acidified with 2 N hydrochloric acid. 1-(2-Mercapto-4-methoxyphenyl)-5-carboxypyrimidine-2,6-dione is obtained in a yield of 14.7 g. (70% of theory). According to the melting point and the IR, UV and NMR spectra, the product is identical with the compound prepared according to Variant I.

B. Ring closure to give 7-methoxy-1-oxo-1H-pyrimido-[6,1-b]benzthiazole-4-carboxylic acid.

Variant I.

111.8 g. 1-(2-Mercapto-4-methoxyphenyl)-5-carboxypyrimidine-2,6-dione are cyclized to give the desired compound by heating for 4 hours at 130° C. with 230 g. polyphosphoric acid, with the splitting off of water. The reaction mixture is then mixed with ice and the precipitate obtained is filtered off with suction and taken up in an aqueous solution of sodium hydroxide. Active charcoal is subsequently added to the solution. Thereafter, it is filtered with suction through a Celite filter and the filtrate is mixed with 2 N hydrochloric acid. The precipitated acid is filtered off with suction and, after drying, there are obtained 82.5 g. (78.6% of theory) 7-methoxy-1-oxo-1H-pyrimido[6,1-b]benzthiazole-4-carboxylic acid; m.p. 277°–278° C. (decomp.).

The structure of the product is confirmed by CHNS analysis and from the IR, UV, NMR and mass spectral data. For example the mass spectrum: $M^+276$, (m/e) 232, 205, 217 and 190.

UV spectrum: pH 7 $\lambda_{max.}=359$ m$\mu$ pH 1 $\lambda_{max.}=361$ m$\mu$ pH 13 $\lambda_{max.}=359$ m$\mu$ Variant II.

29.4 g. 1-(2-Mercapto-4-methoxyphenyl)-5-carboxypyrimidine-2,6-dione are boiled for 6 hours in 300 ml. of a semi-concentrated dioxane solution of hydrochloric acid. The 7-methoxy-1-oxo-1H-pyrimido[6,1-b]benzthiazole-4-carboxylic acid which is thereby formed can be obtained in practically quantitative yield by suction filtration of the hot solution. The physical data of the product agree with those of the compound prepared according to Variant I.

Variant III.

117.7 g. 1-(2-Mercapto-4-methoxyphenyl)-5-carboxypyrimidine-2,6-dione are dissolved in 2.3 liters dimethyl formamide and mixed with 25 ml. Amberlyst 15. After stirring for 5 hours at ambient temperature, a further 25 ml. Amberlyst 15 are added to the reaction mixture and the reaction allowed to proceed overnight. The precipitate obtained is filtered off with suction and treated with a 2 N aqueous solution of potassium hydroxide. The ion exchanger is filtered off with suction and the desired 7-methoxy-1-oxo-1H-pyrimido[6,1-b]benzthiazole-4-carboxylic acid precipitated out by the addition of hydrochloric acid. The yield is 102.8 g. (93% of theory); m.p. 276°–278° C. (decomp.).

Ring closure takes place in an analogous manner with the use of the ion exchanger Amberlite IRC 120.

C. Preparation of a salt.

The 7-methoxy-1-oxo-1H-pyrimido[6,1-b]benzthiazole-4-carboxylic acid obtained by the ring closure reaction is mixed with a small excess of aqueous sodium hydroxide solution. The reaction mixture is filtered and then freeze dried to give the sodium salt of 7-methoxy-1-oxo-1H-pyrimido[6,1-b]benzthiazole-4-carboxylic acid in practically quantitative yield. The product has a water content of 10.5%; m.p. >300° C.

EXAMPLE 2

7-Methoxy-1-oxo-1H-pyrimido[6,1-b]benzthiazole-4-carboxylic acid.

36 g. 6-Methoxy-2-aminobenzthiazole (0.2 mol) are mixed with 43.3 g. (0.2 mol) diethyl ethoxymethylenemalonate. A solution is formed at a bath temperature of 110° C. The reaction mixture is slowly heated to 180° C. and the alcohol formed simultaneously distilled off. After 20 minutes, the cooled melt is mixed with 320 ml. ethanol and a solution of 100 g. sodium hydroxide in 1000 ml. water and the reaction mixture then heated under reflux for 1 hour. The greater part of the alcohol is removed in vacuo and the aqueous solution of the intermediate product mixed with 500 ml. concentrated hydrochloric acid. Subsequently, the water is distilled off until the distillation temperature reaches 108° C. (20% hydrochloric acid), then cooled and the precipitate formed isolated and thereafter washed with water and dried at 70° C. The desired 7-methoxy-1-oxo-1H-pyrimido[6,1-b]benzthiazole-4-carboxylic acid is obtained in a yield of 47.9 g. (86.7% of theory). The melting point of 278°–280° C. and the IR spectrum confirm the identity of the product with the compound obtained according to Example 1B.

EXAMPLE 3

8-Methoxy-1-oxo-1H-pyrimido[6,1-b]benzthiazole-4-carboxylic acid.

Diethyl N-(5methoxybenzthiazole-2-yl)-aminomethylene-malonate is, as described in Example 1A, Variant II, heated in a mixture of 10% aqueous sodium hydroxide solution and ethanol. Without isolating the 1-(2-mercapto-5-methoxyphenyl)-5-carboxypyrimidine-2,6-dione formed as intermediate, the reaction mixture is strongly acidified, 8-methoxy-1-oxo-1H-pyrimido[6,1-b]benzthiazole-4-carboxylic acid thereby precipitating out. The precipitate is subsequently stirred for about 1 hour in the acidic medium. After isolation and drying, the product has a melting point of 277°–278° C.

Mass spectrum: $M^+276$, (m/e) 232, 205, 190.

UV spectrum: pH 1 $\lambda_{max.}=368$ m$\mu$ pH 13 $\lambda_{max.}=365$ m$\mu$

EXAMPLE 4

Ethyl-7-methoxy-1-oxo-1H-pyrimido[6,1-b]benzthiazole-4-carboxylate.

20 g. of the sodium salt of 7-methoxy-1-oxo-1H-pyrimido[6,1-b]benzthiazole-4-carboxylic acid prepared according to Example 1C are slurried in 200 ml. hexametapol and mixed at ambient temperature with 23.45 g. ethyl iodide. The reaction mixture is stirred for 80 minutes and the resultant solution poured into 3 liters of water. The precipitate obtained is separated off and, while still moist, boiled with 500 ml. ethanol and brought into solution by the addition of some nitromethane. After cooling, 12.9 g. (63.3% of theory) ethyl 7-methoxy-1-oxo-1H-pyrimido[6,1-b]benzthiazole-4-carboxylate crystallize out; m.p. 231°–232° C.

In an analogous manner, from the sodium salt of 7-methoxy-1-oxo-1H-pyrimido[6,1-b]benzthiazole-4-carboxylic acid and methyl iodide, there is obtained methyl 7-methoxy-1-oxo-1H-pyrimido[6,1-b]benzthiazole-4-carboxylate; m.p. 253°–254° C.

EXAMPLE 5

1-Oxo-1H-pyrimido[6,1-b]benzthiazole-4-carboxylic acid.

A.

1-(2-Mercaptophenyl)-5-carboxypyrimidine-2,6-dione.

According to Example 1A, Variant I, from 4-oxo-4H-pyrimido[2,1-b]benzthiazole-carboxylic acid, there is obtained 1-(2-mercaptophenyl)-5-carboxypyrimidine-2,6-dione in 77.7% yield; m.p. 254°–255° C.

According to Example 1A, Variant II, from diethyl benzthiazol-2-yl-aminomethylenemalonate, there is obtained the same compound in 52% yield: m.p. 254°–255° C.

Mass spectrum: M+264, (m/e) 231, 187, 151

UV (chloroform/methanol): $\lambda_{max.}=277$ m$\mu$ pH 1 $\lambda_{max.}=274$ m$\mu$ pH 13 $\lambda_{max.}=292$ m$\mu$

B. 1-Oxo-1H-pyrimido[6.1-b]benzthiazole-4-carboxylic acid.

According to Example 1B, Variant III, 31.7 g. 1-(2-mercaptophenyl)-5-carboxypyrimidine-2,6-dione in 310 ml. dimethylformamide are stirred for 12 hours at ambient temperature after the addition of a total of 40 ml. Amberlite Amberlyst 15. After working up in the manner described in Example 1B, Variant III, there are obtained 20.8 g. (70.4% of theory) 1-oxo-1H-pyrimido[6,1-b]-benzthiazole-4-carboxylic acid; m.p. 278°–279° C. (decomp.).

Mass spectrum: M+246, (m/e) 202, 175, 160

NMR (DDMSO): 3H, 8.86 ppm.

UV spectrum: pH 7 $\lambda_{max.}=356$ m$\mu$ pH 13 $\lambda_{max.}=358$ m$\mu$

The ring closure can also be carried out by heating with 20% hydrochloric acid.

C. Analogously to Example 1C, there is prepared a sodium salt (water content 8%); m.p. >300° C.

In an analogous manner, there are obtained:

(a) from ethyl 8-ethoxy-4-oxo-4H-pyrimido[2,1-b]benzthiazole-3-carboxylate, via 1-(2-mercapto-4-ethoxyphenyl)-5-carboxypyrimidine-2,6-dione (yield 86.9% of theory) m.p. 272°–275° C.), 7-ethoxy-1-oxo-1H-pyrimido[6,1-b]benzthiazole-4-carboxylic acid (yield 74.5% of theory; m.p. 264°–265° C.).

UV spectrum: pH 7 $\lambda_{max.}=359$ m$\mu$ pH 1 $\lambda_{max.}=361$ m$\mu$ pH 13 $\lambda_{max.}=359$ m$\mu$ Mass spectrum M+290, (m/e) 246, 219, 204.

By the addition of a small excess of 1 N aqueous potassium hydroxide solution and subsequent freeze drying, there is obtained the potassium salt of 7-ethoxy-1-oxo-1H-pyrimido[6,1-b]benzthiazole-4-carboxylic acid (water content 5.6%); m.p. >300° C.

(b) from ethyl 8-hydroxy-4-oxo-4H-pyrimido[2,1-b]benzthiazole-3-carboxylate, via 1-(2-mercapto-4-hydroxyphenyl)-5-carboxypyrimidine-2,6-dione (yield 60.7% of theory; m.p. 230°–232° C.), 7-hydroxy-1-oxo-1H-pyrimido[6,1-b]-benzthiazole-4-carboxylic acid (yield 51.1% of theory; m.p. 280°–281° C.).

Mass spectrum; trimethylsilyl derivative M+406 (m/e) 391, 364, 263, 188, 153

UV spectrum: pH 7 $\lambda_{max.}=360$ m$\mu$ pH 1 $\lambda_{max.}=364$ m$\mu$ pH 13 $\lambda_{max.}=376$ m$\mu$ For the preparation of the potassium salt, the acid is mixed with a small excess of aqueous potassium bicarbonate solution. The solution is filtered and the potassium salt is isolated by freeze drying; m.p. >300° C.

(c) from ethyl 7,8-methylenedioxy-4-oxo-4H-pyrimido[2,1-b]-benzthiazole-3-carboxylate, via 1-(2-mercapto-4,5-methylenedioxyphenyl)-5-carboxypyrimidine-2,6-dione (yield 70.3% of theory; m.p. 273°–275° C.), 7,8-methylene-dioxy-1-oxo-1M-pyrimido[6,1-b]benzthiazole-4-carboxylic acid (yield 71.7% of theory; m.p. 283°–284° C. (decomp.)).

Mass spectrum: M+290, (m/e) 246, 219, 204.

(d) from ethyl 7,8-dimethyl-4-oxo-4H-pyrimido[2,1-b]-benzthiazole-3-carboxylate, via 1-(2-mercapto-4,5-dimethylphenyl)-5-carboxypyrimidine-2,6-dione (yield 89.7% of theory; m.p. 258°–259° C. (decomp.); mass spectrum: M+292, (m/e) 259, 215, 179, 151), 7,8-dimethyl-1-oxo-1H-pyrimido[6,1-b]benzthiazole-4-carboxylic acid (yield 56.2% of theory; m.p. 280°–281° C.).

Mass spectrum: M+274, (m/e) 230, 203, 188

NMR (DDMSO): 3H, 8.81 ppm

UV spectrum: pH 1 $\lambda_{max.}=363$ m$\mu$ pH 13 $\lambda_{max.}=361$ m$\mu$ (e) from ethyl 8-methyl-4-oxo-4H-pyrimido[2,1-b]benzthiazole-3carboxylate, via 1-(2-mercapto-4-methylphenyl)-5-carboxypyrimidine-2,6-dione (yield 77.7% of theory; m.p. 258°–260° C.), 7-methyl-1-oxo-1H-pyrimdio[6,1-b]-benzthiazole-4-carboxylic acid (yield 63% of theory; m.p. 262°–264° C.).

Mass spectrum: M+260, (m/e) 216, 189, 174

NMR (DDMSO): 3H, 8.83 ppm

UV (DMF+Methanol): $\lambda_{max.}=360$ m$\mu$ pH 7 $\lambda_{max.}=360$ m$\mu$ pH 1 $\lambda_{max.}=354$ m$\mu$ pH 13 $\lambda_{max.}=359$ m$\mu$ (f) from ethyl 8-chloro-4-oxo-4H-pyrimido[2,1-b]benzthiazole-3-carboxylate, via 1-(2-mercapto-4-chlorophenyl)-5-carboxypyrimidine-2,6-dione, 7-chloro-1-oxo-1H-pyrimido-[6,1-b]benzthiazole-4-carboxylic acid (yield 60% of theory; m.p. 264°–265° C.).

Mass spectrum: M+280, (m/e) 236, 209, 194

(g) from 7,9-dimethyl-8-methoxy-4-oxo-4H-pyrimido-[2,1-b]benzthiazole-3-carboxylate (m.p. 146°–148° C.), via 1-(2-mercapto-3,5-dimethyl-4-methoxyphenyl)-5-carboxypyrimidine-2,6-dione (quantitative yield; m.p. 249°–250° C.; UV (methanol): $\lambda_{max.}$: 273 m$\mu$; pH1 $\lambda_{max.}=271$ m$\mu$; pH 13 $\lambda_{max.}=291$ m$\mu$), 6,8-dimethyl-7-methoxy-1-oxo-1H-pyrimido[6,1-b]benzthiazole-4-carboxylic acid (yield 58.8% of theory; m.p. 269°–272° C.).

Mass spectrum: M+304, (m/e) 260, 245, 233, 218, 203

UV (methanol+DMF): $\lambda_{max.}=366$ m$\mu$ pH 1 $\lambda_{max.}=65$ m$\mu$ pH 13 $\lambda_{max.}=364$ m$\mu$ (h) from ethyl 7,8-dimethoxy-4-oxo-4H-pyrimido[2,1-b]-benzthiazole-3-carboxylate, via 1-(2-mercapto-4,5-dimethoxyphenyl)-5-carboxypyrimidine-2,6-dione (quantitative yield), 7,8-dimethyl-1-oxo-1H-pyrimido[6,1-b]benzthiazole-4-carboxylic acid (yield 53.9% of theory; m.p. 260°–261° C. (decomp.)).

Mass spectrum: M+ 306

Potassium salt: UV (water): $\lambda_{max.}=371$ m$\mu$ pH 1 $\lambda_{max.}=388$ m$\mu$ pH 13 $\lambda_{max.}=369$ m$\mu$ pH 7 $\lambda_{max.}=371$ m$\mu$ (i) from ethyl 8-methylthio-4-oxo-4H-pyrimido[2,1-b]benzthiazole-3-carboxylate, via 1-(2-mercapto-4-methylthiophenyl)-5-carboxypyrimidine-2,6-dione (quantitative yield; mass spectrum: M+ 310, 292; UV (methanol) $\lambda_{max.}=262$ m$\mu$; pH 1 $\lambda_{max.}=265$ m$\mu$; pH 13 $\lambda_{max.}=276$ m$\mu$), 7-methylthio-1-oxo-1H-pyrimido[6,1- b]benzthiazole-4-carboxylic acid (yield 73% of theory; m.p. 260°–261° C.)

Mass spectrum: M+ 292

UV spectrum: pH 13 $\lambda_{max.}=363$ mμ pH 1 $\lambda_{max.}=369$ mμ

(j) from ethyl 8-isopropyl-4-oxo-4H-pyrimido[2,1-b]benzthiazole-3-carboxylate, via 1-(2-mercapto-4-isopropyl-phenyl)-5-carboxypyrimidine-2,6-dione, 7-isopropyl-1-oxo-1H-pyrimido[6,1-b]benzthiazole-4-carboxylic acid; m.p. 240°–241° C.

EXAMPLE 6

8-Nitro-1-oxo-1H-pyrimido[6,1-b]benzthiazole-4-carboxylic acid 5.52 g. 1-Oxo-1H-pyrimido[6,1-b]benzthiazole-4-carboxylic acid (prepared according to Example 5) are introduced into a mixture of 27.5 ml. concentrated sulphuric acid and 27.5 ml. 96% nitric acid at 0°–5° C. The reaction mixture is stirred for 1 hour at 0° C. and then for 15 minutes at ambient temperature and thereafter the reaction mixture is poured on to ice. The precipitate obtained is subsequently filtered off and recrystallized from a mixture of ethanol/dimethylformamide. There are obtained 3.6 g. 8-nitro-1-oxo-1H-pyrimido[6,1-b]benzthiazole-4-carboxylic acid (62.1% of theory); m.p. 277°–278° C.

This product is neutralized, analogously to Example 1C, with a 1 N aqueous solution of potassium hydroxide and, by freeze drying, the corresponding potassium salt is isolated (6% water content).

EXAMPLE 7

N-(5-Tetrazolyl)-7-methoxy-1-oxo-1H-pyrimido[6,1-b]benzthiazole-4-carboxamide 5.52 g. 7-Methoxy-1-oxo-1H-pyrimido[6,1-b]benzthiazole-4-carboxylic acid (prepared according to Example 1) in 150 ml. dimethylformamide are mixed with 7.14 g. N,N'-carbonyldiimidazole. The reaction mixture is subsequently stirred for 90 minutes at 100° C. and for 1 hour at ambient temperature, then mixed with 2.26 g. 5-aminotetrazole monohydrate and again heated for 3 hours at 100° C. The solvent is substantially removed in vacuo and the residue stirred with water. The precipitate consists of 5.2 g. N-(5-tetrazolyl)-7-methoxy-1-oxo-1H-pyrimido[6,1-b]benzthiazole-4-carboxamide (75.7% of theory); m.p. 234°–235° C. (recrystallized from nitromethane).

Titration in dimethylformamide with 0.1 N tetrabutyl ammonium hydroxide: equivalent weight 343.

By neutralization with 1 N aqueous potassium hydroxide solution and subsequent freeze drying, there is isolated the corresponding potassium salt.

UV (water) $\lambda_{max.}=346$ mμ pH 1 $\lambda_{max.}=357$ mμ pH 13 $\lambda_{max.}=346$ mμ

EXAMPLE 8

N-(5-Tetrazolyl)-1-oxo-1H-pyrimido[6,1-b]benzthiazole-4-carboxamide

In a manner analogous to that described in Example 7, from 4.9 g. 1-oxo-1H-pyrimido[6,1-b]benzthiazole-4-carboxylic acid (prepared according to Example 5), 3.6 g. N,N'-carbonyldiimidazole and 1.9 g. anhydrous aminotetrazole, there is obtained N-(5-tetrazolyl)-1-oxo-1H-pyrimido[6,1-b]benzthiazole-4-carboxamide. The yield is 80.3% of theory; m.p. 243°–244° C.

By titration with 1 N aqueous potassium hydroxide solution and subsequent freeze drying of the aqueous solution, there is prepared the corresponding potassium salt.

With respect to the proper dosage and methods of application for the instant compounds, these are comparable to those for the commercially known compound "Fragivix", i.e. 2-ethyl-3-(4'-hydroxybenzoyl)-benzofuran. They can also be administered per os. The instant compounds make possible comprehensive therapy of acute as well as chronic phlebological and capillary afflictions as well as varicose syndromes. The instant compunds retard reactions leading to edemas and swellings, including those of allergic origin.

The typical daily dosage of 10 to 300 mg results in reducing or eliminating the above afflictions, commonly within some days. A preferred dosage is 30–100 mg.

The superior activity of the novel compounds is shown by comparing the inhibition of the passive cutaneous anaphylactic reaction in rats produced by injection of serum containing reaginic antibodies to egg albumin. Hetrazan, i.e. 1-diethylcarbamoyl-4-methylpiperazine, was used as a comparison compound. Specifically, tests were run as follows:

Serum containing reaginic (IgE-like) antibody to egg albumin was prepared by injecting rats intramuscularly with 0.1 ml of a solution of the antigen (10 mg/ml) in saline together with 0.5 ml of Bordetella pertussis vaccine (Behring; $2\times10^{10}$ organisms/ml). 9–14 Days later the animals were bled from the abdominal aorta; the serum was pooled and stored at −20° until required. The titer of the serum, i.e. the highest dilution inducing passive cutaneous anaphylaxis (PCA) in the rat following a 48-hour latent period, was between 1:8 and 1:32. For use in these experiments the serum was diluted 1:24. The reaginic nature of the antibody was demonstrated by its ability to induce PCA with a latent period in excess of 7 days and also by abolition of its PCA activity by heating it at 56° C. for 1 hour.

The animals were anesthetized with 2,2-dichloro-1,1-difluoroethyl-methyl ether, sold under the trademark Penthrane, and were sensitized by injecting 0.1 ml of the antiserum into the shaved abdominal flanks. After 48 hours for reaginic PCA, the animals were given an intravenous injection of 1 ml of saline solution containing 0.5% by weight of egg albumin and 0.25% by weight of Evans blue.

After having killed and exsanguinated the animals, the size in square millimeters and the intensity, in arbitary scores, of the resulting blue spot were determined. The product of these two parameters was used to determine the degree of the reaction and the degree of reaction with no active material was taken as the standard against which to measure % inhibition of the anaphylactic reaction.

6 Animals were used per dose level and for control.

The test material was given per os or injected intravenously (i.v.) immediately before the antigen, using a solution in water containing 0.5% HCl and 2% of dimethylformamide. The volume of the application was varied to give the indicated dosage of active material. The results obtained were as follows:

TABLE

Homologous PCA reaction in rats induced by reaginic antibodies (Ovalbumin 2 × cryst. and Bord.pertussis 2 × 10$^{10}$)
Application of the compounds : p.o. and i.v. immediately before Antigen
6 rats/dose and 6 controls

| | Active Material | dose mg/kg p.o. | % inhibition of PCA | dose mg/kg i.v. | % inhibition of PCA |
|---|---|---|---|---|---|
| | HETRAZAN | >60 | <10 | 52 | 58 |
| Example 1 | | | | 0.02 | 56 |
| 3 | | 3.0 | 24 | 1.5 | 100 |
| 5 | | 3.0 | 26 | | |
| 5(a) | | 3.0 | 78 | | |
| 5(b) | | 3.0 | 34 | | |
| 5(d) | | 3.0 | 90 | | |
| 5(e) | | 1.5 | 63 | | |
| 5(f) | | 3.0 | 13 | | |
| 5(g) | | | | 0.75 | 55 |
| 5(h) | | 3.0 | 23 | | |
| 5(i) | | 3.0 | 48 | | |
| 6 | | 3.0 | 30 | | |
| 7 | | | | 3.0 | 45 |

These pharmacological data show that the novel compounds exert a far stronger antianaphylactoid activity than Hetrazan whether administered intravenously or per os.

It will be appreciated that the instant specification and examples are set forth by way of illustration and not limitation, and that various modifications and changes may be made without departing from the spirit and scope of the present invention.

What is claimed is:

1. A 1-oxo-1H-pyrimido[6,1-b]benzthiazole of the formula

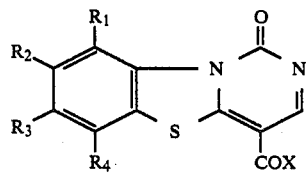

wherein
$R_1$, $R_2$, $R_3$ and $R_4$ each independently is hydrogen, halogen, hydroxy, nitro, trifluoromethyl, or alkyl, alkoxy or alkylthio containing up to 6 carbon atoms, or
$R_2$ and $R_3$ together are alkylenedioxy containing up up to 3 carbon atoms, and
X is hydroxy, alkoxy containing up to 6 carbon atoms or tetrazolyl-5-amino,
or a pharmacologically acceptable salt thereof.

2. A compound according to claim 1, wherein
$R_1$, $R_2$, $R_3$ and $R_4$ each independently is hydrogen, halogen, hydroxy, nitro, trifluoromethyl, or alkyl, alkoxy or alkylthio of up to 4 carbon atoms, or
$R_2$ and $R_3$ together are methylenedioxy, and
X is hydroxy, alkoxy of up to 4 carbon atoms or tetrazolyl-5-amino.

3. A compound according to claim 1, wherein such compound is 7-methoxy-1-oxo-1H-pyrimido[6,1-b]benzthiazole-4-carboxylic acid of the formula

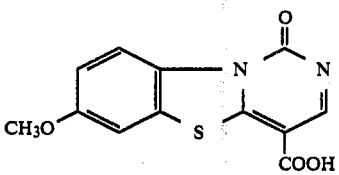

4. A compound according to claim 1, wherein such compound is 7,8-dimethyl-1-oxo-1H-pyrimido[6,1-b]benzthiazole-4-carboxylic acid of the formula

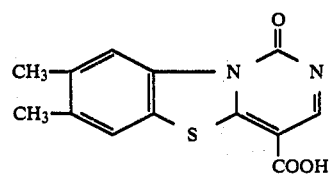

5. A compound according to claim 1, wherein such compound is 7-methyl-1-oxo-1H-pyrimido[6,1-b]benzthiazole-4-carboxylic acid of the formula

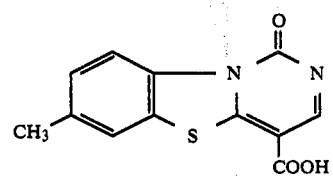

6. A compound according to claim 1, wherein such compound is 6,8-dimethyl-7-methoxy-1-oxo-1H-pyrimido[6,1-b]benzthiazole-4-carboxylic acid of the formula

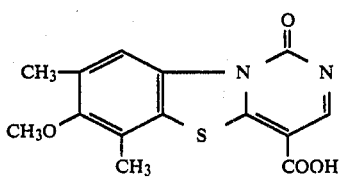

7. A compound according to claim 1, wherein X is hydroxy.

8. An anti-allergy pharmaceutical composition comprising a physiologically acceptable diluent and an anti-allergically effective amount of a compound according to claim 1.

9. A method of inhibiting an allergic rection in a patient comprising administering to such patient an anti-allergically effective amount of a compound according to claim 1.

10. The method according to claim 9, wherein such compound is
7-methoxy-1-oxo-1H-pyrimido[6,1-b]benzthiazole-4-carboxylic acid,
7,8-dimethyl-1-oxo-1H-pyrimido[6,1-b]benzthiazole-4-carboxylic acid,
7-methyl-1-oxo-1H-pyrimido[6,1-b]benzthiazole-4-carboxylic acid, or
6,8-dimethyl-7-methoxy-1-oxo-1H-pyrimido[6,1-b]benzthiazole-4-carboxylic acid.

* * * * *